United States Patent [19]
Augustine et al.

[11] Patent Number: 6,010,528
[45] Date of Patent: Jan. 4, 2000

[54] SUPPORT APPARATUS WHICH CRADLES A BODY PORTION FOR APPLICATION OF LOCALIZED COOLING TO HIGH CONTACT-PRESSURE BODY SURFACE AREAS

[75] Inventors: Scott D. Augustine, Bloomington; Paul Anthony Iaizzo, White Bear Lake; Ephraim M. Sparrow, St. Paul; Paul Steven Johnson, White Bear Lake; Randall C. Arnold, Minnetonka, all of Minn.

[73] Assignee: Augustine Medical, Inc., Eden Prairie, Minn.

[21] Appl. No.: 08/704,932

[22] Filed: Aug. 30, 1996

[51] Int. Cl.⁷ .................................................... A61F 7/00
[52] U.S. Cl. ......................... 607/104; 607/108; 607/114; 297/452.21; 5/421
[58] Field of Search ................... 607/96, 104, 108–112, 607/114; 297/284.6, 452.21, 452.27, 452.41, 452.57, 458–459; 5/421–423, 449–455; 126/204; 165/46

[56] References Cited

U.S. PATENT DOCUMENTS

| | | |
|---|---|---|
| 3,289,748 | 12/1966 | Jennings . |
| 3,738,702 | 6/1973 | Jacobs ..................................... 165/105 |
| 4,026,299 | 5/1977 | Sauder .................................... 128/400 |
| 4,114,620 | 9/1978 | Moore et al. ............................ 128/254 |
| 4,149,541 | 4/1979 | Gammons et al. ...................... 128/400 |
| 4,416,281 | 11/1983 | Cooper et al. .......................... 128/400 |
| 4,706,672 | 11/1987 | Jones ....................................... 128/379 |
| 4,788,730 | 12/1988 | Bexton ........................................ 5/454 |
| 4,844,072 | 7/1989 | French et al. ........................... 128/400 |
| 4,884,304 | 12/1989 | Elkins ..................................... 5/421 X |
| 4,962,761 | 10/1990 | Goldent ................................... 128/400 |
| 4,966,145 | 10/1990 | Kikumoto et al. ...................... 128/377 |
| 5,072,875 | 12/1991 | Zacoi ...................................... 128/400 |
| 5,097,829 | 3/1992 | Quisenberry ........................ 607/104 X |
| 5,138,138 | 8/1992 | Theilacker et al. ..................... 219/528 |
| 5,169,384 | 12/1992 | Bosniak et al. ............................ 604/20 |
| 5,174,285 | 12/1992 | Fontenot ................................. 128/400 |
| 5,176,424 | 1/1993 | Tobita et al. ............................ 297/284 |
| 5,183,039 | 2/1993 | Sarian et al. ............................ 128/400 |
| 5,269,369 | 12/1993 | Faghri ...................................... 607/104 |
| 5,344,436 | 9/1994 | Fontenot et al. ........................ 607/104 |
| 5,395,162 | 3/1995 | Jay et al. ............................ 297/452.41 |
| 5,433,083 | 7/1995 | Kuramarohit ............................. 62/259 |
| 5,448,788 | 9/1995 | Wu ............................................. 5/421 |
| 5,456,701 | 10/1995 | Stout .................................. 607/104 X |
| 5,486,206 | 1/1996 | Avery ..................................... 607/104 |

OTHER PUBLICATIONS

"Prevention of Pressure Ulcers by Focal Cooling: Histological Assessment in a Porcine Model", Paul A. Iaizzo, Ph.D. et al., *Wounds: A Compendium of Clinical Research and Practice*, Sep./Oct. 1995, vol. 7, No. 5, pp. 161–169.

"Designed By Critical Care Physicians And Nurses With The Patient In Mind" brochure, Triadyne by KCI.

*Primary Examiner*—Cary O'Connor
*Assistant Examiner*—Ryan Carter
*Attorney, Agent, or Firm*—Gary Cary Ware Freidenrich

[57] ABSTRACT

A weight-bearing apparatus such as a cushion, prosthetic device or bed mattress includes a support surface having a shaped or sculpted portion that conforms to the shape of a body portion being supported. The shaped portion fits to the body portion, thereby to position the body portion so as to situate one or more weight-bearing parts of the body portion over specific zones of the support surface that are cooled below normal body temperature. The reduced temperature applied to the zones of the support surface removes heat from the weight-bearing areas, thereby reducing, the risk of injury to tissue in those areas.

19 Claims, 7 Drawing Sheets

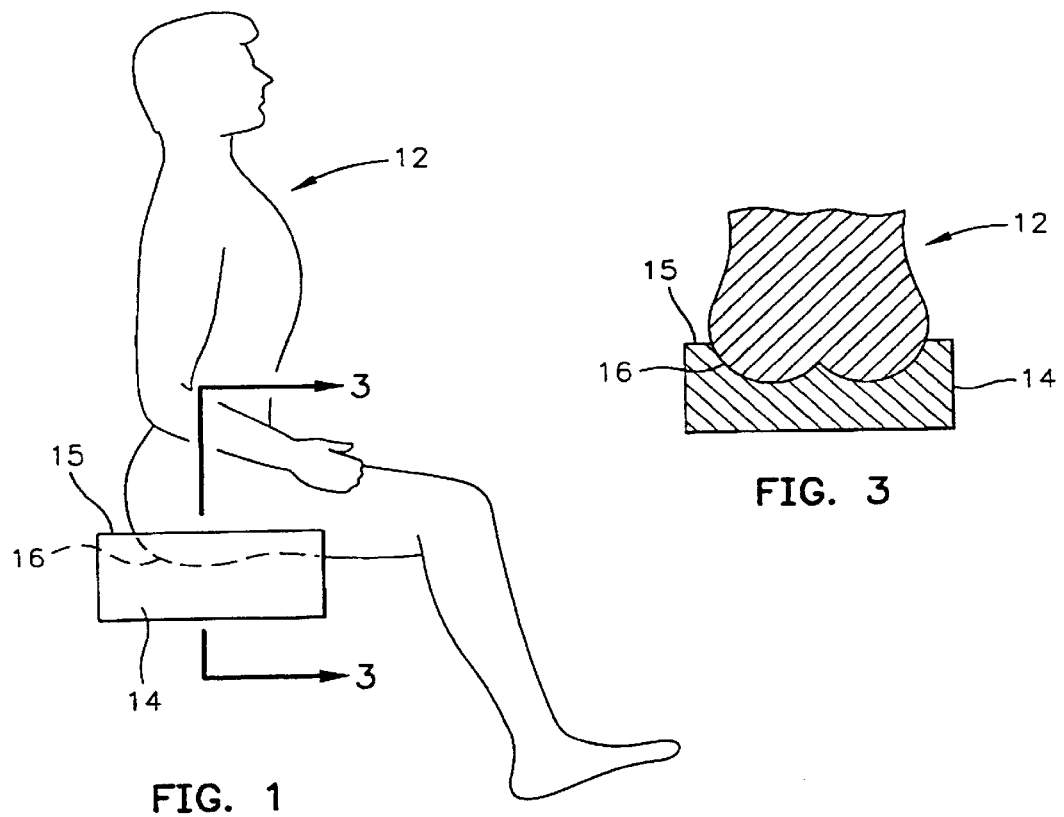
FIG. 1
FIG. 3
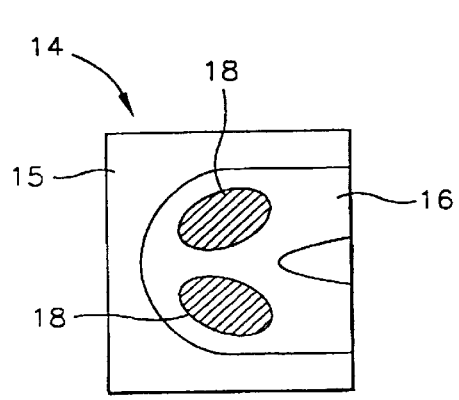
FIG. 2
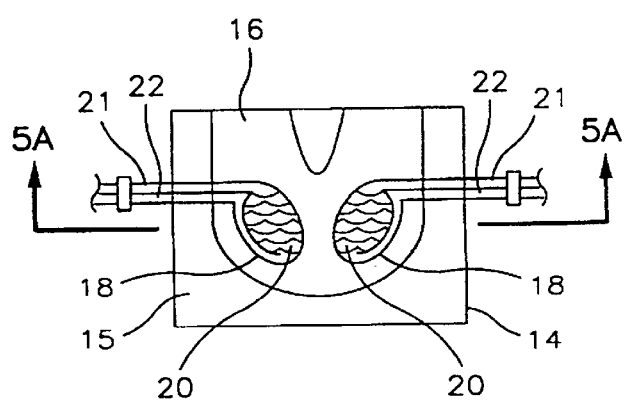
FIG. 4

SUPPORT APPARATUS WHICH CRADLES A BODY PORTION FOR APPLICATION OF LOCALIZED COOLING TO HIGH CONTACT-PRESSURE BODY SURFACE AREAS

BACKGROUND OF THE INVENTION

1. Field of the Invention

The invention concerns an apparatus that supports at least a portion of a human or animal body ("body portion") while applying cooling to a weight-bearing area of the body portion that is supported by the apparatus. More specifically, the invention concerns an apparatus having a shaped portion that fits to a corresponding shape of the body portion and applies cooling to one or more weight-bearing areas of the body portion to prevent or ameliorate tissue damage resulting from heat and pressure.

The application of pressure to the skin of a patient for a prolonged period of time has been known to cause pressure ulcers. The weight-bearing areas of the body surface are exposed to pressures that can easily exceed 100 mmHg (torr.). It has been shown that blood flow ceases in capillaries that are exposed to compressive pressures exceeding 25 torr. Therefore, the weight-bearing areas of the body surface and subcutaneous tissue can be expected to have inadequate blood flow or even a complete lack of blood flow during the time the weight is borne.

Normal cellular metabolism depends on adequate circulation of blood to deliver oxygen, nutrients and to remove waste products. Prolonged interference with the local circulation results in a two-part sequence of events, beginning with ischemia (a severe reduction of blood and oxygen supply to the tissues), and terminating in necrosis (irreversible death of the cells and tissues, resulting in sloughing).

People normally will shift their positions in a chair or get up and walk around to relieve the pressure on their buttocks. People normally will regularly roll over in bed while sleeping to periodically redistribute their weight to a different surface area. This movement is usually in response to pain or discomfort caused by the tissue ischemia of the weight-bearing skin, subcutaneous or deeper-tissue. Bed-ridden or wheelchair-ridden patients or patients on operating room tables may not be aware of the ischemic pain if they have brain or spinal cord injury, :stroke injury, dementia, prolonged surgery under anesthesia, or prolonged sedation and mechanical ventilation. Alternatively, severe illness, neuromuscular diseases or nervous system injury may prevent patients from moving even if they are aware of the ischemic pain.

The incidence of pressure ulcers in surgical patients varies from 12% to 66% in different studies. Surveys of general hospital patients indicate that 3–4.5% of all patients develop pressure ulcers during hospitalization. Pressure ulcers usually develop near regions of the body which have a bony prominence near the skin. More than 80% of all pressure ulcers occur at the following five locations:

1. Sacro-coccygeal region (high buttocks), supine position.
2. Greater trochanter (low hip), lateral recumbent position.
3. Ischial tuberosity (low buttocks), sitting position.
4. Tuberosity of the calcaneus (heel), supine position.
5. Lateral malleolus (outer ankle), lateral recumbent position.

Surgical and bed ridden patients are not the only patients susceptible to pressure ulcer development. For example, paralyzed patients spend much of their lifetime in a wheelchair. One study indicated that the incidence of pressure ulcers is 21.6% for paraplegics and 23.1% for quadriplegics.

Equipment for pressure ulcer prevention has focused in three areas:

1. Regular turning or movement of the patient to minimize the duration of time that pressure is applied to any give surface area. The tissue is allowed time to re-perfuse during the period that the pressure is not applied.
2. Passive support surfaces (cushions, mattresses and pads of all kinds), which may utilize unique or special materials or shapes to minimize the pressure exerted against any given point of the body surface. Many types of materials have been tried including; different types of polymeric foam, polymeric gels, water and air filled bladders.
3. Active support surfaces such as a series of air filled bladders that alternately inflate and deflate to automatically redistribute the pressure.

Considering the high incidence of pressure ulcers despite the availability of these many passive support surfaces (various materials and shapes), it is clear that simply distributing the pressure to a larger surface area, in and of itself will not effectively prevent pressure ulcers. Although active support surfaces have been used to prevent pressure ulcers, it is clear however that they are very expensive, cumbersome and noisy. Therefore active support surfaces are not likely to be used in many pressure ulcer prevention situations.

Finally, aside from the obvious pain and health risk to the patient (having a chronic infection in a chronic open wound), pressure ulcers are extremely expensive and slow to heal. Healing the average pressure ulcer costs $30,000 to $40,000 and takes about 3 to 6 months. The high incidence of pressure ulcers, the lack of any proven method of preventing pressure ulcers and the extremely high cost of healing a pressure ulcer once it develops, clearly indicates a significant need for a new technology.

It is reasonable to assume that heat should be an important factor in the formation of pressure ulcers. All tissues increase their metabolic rates 7–10% for each 1° C. increase in temperature. The increased metabolic rate increases the demand of the cells for oxygen a similar 7–10% for each 1° C. increase in temperature. In a patient whose tissue perfusion is already compromised by external pressure or by vascular insufficiency, this increased metabolic demand for oxygen could increase the rate of tissue injury. We hypothesized that this increased metabolic demand was the cause of the frequent "burns" observed after water mattress warming therapy during surgery, despite relatively the low temperatures (39°–42° C.) of the mattresses. These low temperature injuries may result in full thickness skin damage which appears identical to third degree burns resulting from exposure of the skin to high temperatures. While the full thickness damage to the skin is identical to a high temperature thermal injury ("burn"), in reality the injury is caused by pressure necrosis which is accelerated due to the increased metabolic rate of the tissue. While this interrelationship between temperature, pressure and tissue ischemia is scientifically logical it had never been proven prior to our recent experiments.

Further, it has been known that hypothermia decreases the cellular metabolic rate and increases the tolerance of cells to periods of inadequate blood flow. This is the reason that patients are cooled during cardiac bypass. WE therefore hypothesized that cooling the skin and subcutaneous tissue would effectively prolong the time to injury, in the face of the ischemia caused by an inadequate local blood flow resulting from pressure exerted against that tissue.

To test these hypotheses, we developed a porcine model to investigate pressure ulcer formation. Twelve metal discs were applied to the back of an anesthetized swine. The pressure on the skin under each disc was approximately 100 torr (totally occlusive to blood flow), for a 10 hour period of time. The temperature of the discs was carefully controlled at 25° C., 35° C., 40° C. and 45° C. Normal porcine temperature is 38° C.(Normal human body temperature is 37° C.) The severity of the resultant tissue injuries directly correlated with an increase in temperature. No tissue damage was found under the 25° C. discs. Severe damage of the skin, subcutaneous and deep tissues was found under the 45° C. discs. The 35° and 40° C. discs also caused severe damage, but intermediate to the extreme temperatures. The results of this experiment proved for the first time (that we are aware of), that both of our hypotheses were correct:

1. Even mild heat will accelerate the rate of tissue injury due to pressure induced ischemia.
2. Mild cooling will protect tissue from injury due to pressure induced ischemia.

Water mattresses circulating cool or even cold water have been used for decades to cool febrile patients. However, experience shows that the application of cold to widespread surface areas of the body is both extremely uncomfortable and will cause hypothermia and shivering.

2. Description of the Related Art

In the prior art, U.S. Pat. No. 3,738,702 discloses a seat structure that cools a portion of the human body that rests against the seat in response to the heat of the body, where the body engages the seat. In order to maximize the sensitivity of the cooler to body heat, the cooler is placed as near as possible to the surface of the seat contacted by the body.

SUMMARY OF THE INVENTION

The object of this invention is to provide a weight-bearing apparatus such as a chair or wheelchair cushion, a prosthetic device, or a bed cushion, having a support surface that will prevent pressure ulceration. The support surface has a shaped or sculpted portion that conforms to the shape of a body portion being supported. In this respect, the shaped portion cradles the body portion by inhibiting lateral motion of the body portion on the support surface. This surface portion fits to the body portion, thereby to position the body portion so that the weight-bearing part(s) of the body portion, specifically areas of predictable "high" pressure contact (greater than 20–25 torr, for example), are situated on or over one or more specific parts ("zones") of the support surface cooled below normal body temperature. The support surface applies a reduced temperature to (or, more precisely, removes heat from) those zones of the support surface that are acted on by specific body areas predicted to be in "high" pressure contact with the surface, in order to remove heat from those body areas.

Metabolic heat generated by ischemic tissue is trapped by insulating cushions and raises the tissue temperature. The metabolic heat cannot be internally removed because of the inadequate blood flow and cannot be externally removed because of the thermal insulation characteristics of the padded cushions or mattresses. The metabolism continues (anaerobically) despite the inadequate blood flow and the heat generated by this metabolism continues to accumulate. Our swine studies show that any warming of tissue is clearly harmful and cooling of the tissue below body temperature is beneficial in preventing pressure injury to tissue. Cooling below normal body temperature will be beneficial. Therefore this invention prevents the buildup of naturally generated metabolic body heat in the ischemic tissue.

The invention will not cool body surface areas which do not experience high pressure contact. Because of the minimal blood flow in the areas of high pressure, the cooling applied there will be substantially isolated to those tissues and will not cause general hypothermia or discomfort.

Therefore, the principal object of this invention is to provide a support apparatus that locally cools body portion surface areas subject to high contact pressure.

Another objective is to provide a support apparatus having a support surface with a shaped contoured, or sculpted portion for retaining a body portion while cooling weight-bearing areas of the body portion that is retained within the surface portion.

A further objective is to afford a support surface of a support apparatus with a means for retaining a body portion at the surface and a means for applying localized cooling to weight-bearing areas of the body portion that experience high contact pressure.

Other objectives and advantages will be manifest when the following detailed description is read in conjunction with the below-described.

BRIEF DESCRIPTION OF THE DRAWINGS

FIG. 1 is a side view of a person seated on a cushion that illustrates the invention.

FIG. 2 shows a top, plan view of the cushion that is illustrated in FIG. 1, showing a support surface.

FIG. 3 is a cross-section of the seated patient taken at section 3—3 of FIG. 1.

FIG. 4 is a partially schematic illustration of the support cushion of FIG. 2.

DETAILED DESCRIPTION OF THE PREFERRED EMBODIMENTS

Figure 5A:
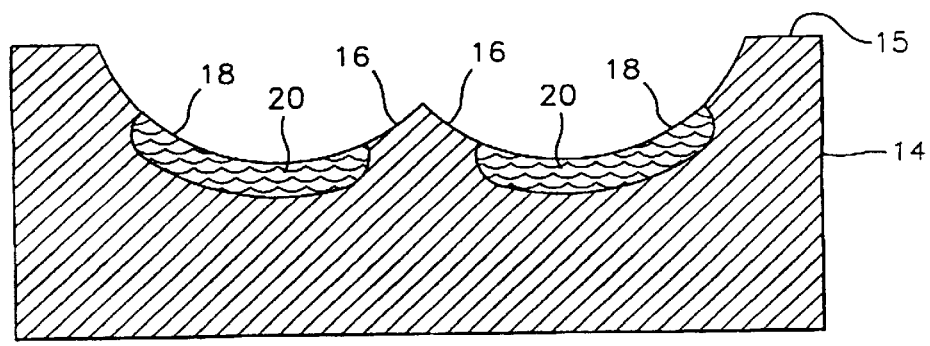
FIGS. 5A and 5B are respective cross-sections at B—B in FIG. 4 of the preferred embodiment.

With reference now to the figures in which like reference numerals indicate like elements throughout the drawings, illustrations of our invention will be found. Our invention is a weight-bearing apparatus having a support surface with a shaped portion that conforms to the shape of a body portion being supported. The shaped portion of the surface includes one or more zones. The zones interface with weight-bearing areas of the body portion that are at risk of pressure injury. The zones are cooled to below body temperature in order to reduce or eliminate the risk of injury. The illustrations show our invention embodied in a support cushion or pad as might be used, for example, in a chair or wheelchair to support a portion of a human or animal body (hereinafter "body portion"), and in a prosthesis for supporting a body portion remaining alter amputation.

The support cushion that embodies our invention is illustrated in FIGS. 1–3 where a person 12 is seated on a cushion 14 having a support surface 15 which supports a portion of the person's body. As FIGS. 1 and 3 clearly show, the body portion that is supported comprises the buttocks and back surfaces of the person's upper legs. As is best seen in FIG. 2, at least a portion of the support surface 15 is sculpted into a shape that accommodates the shape of a body portion being supported. In particular, the sculpted portion, indicated by reference numeral 16, of the surface has a shape much like a tractor seat that inhibits lateral motion of the body portion on the surface. Thus, when seated in the sculpted portion 16 of the support surface 15, the person will always be positioned in substantially the same location on the cushion 14. In the support cushion embodiment of the invention, the sculpted portion 16 of the support surface 15 therefore embodies a positioning means for receiving and fitting to a portion of a human body. In the instance illustrated in FIGS. 1–3, that portion is the buttocks and rear surfaces of the upper thighs. Of course, the support cushion may be made in various sizes in order to fit a variety of persons.

The weight-bearing ischial tuberosities of person 12 (such as the bones in the buttocks) and the skin areas containing the adjacent, predictably ischemic tissue can be anticipated in the sculpted portion 16. Such areas correspond to zones of high pressure contact between the body portion of the person 12 and the support surface 15. These zones are identified by reference numeral 18 in FIG. 2. In the invention, these zones of high pressure contact are cooled by a cooling means.

As can be appreciated from FIG. 3, the cushion 14 may be manufactured from a compressible material that "remembers" its uncompressed shape, and resumes that shape when freed from compression. However, in the invention, the uncompressed shape exhibits the sculpted area 16 of the support surface 15 having a shape corresponding to the portion of the human body being supported by the cushion 14.

Figure 5B:
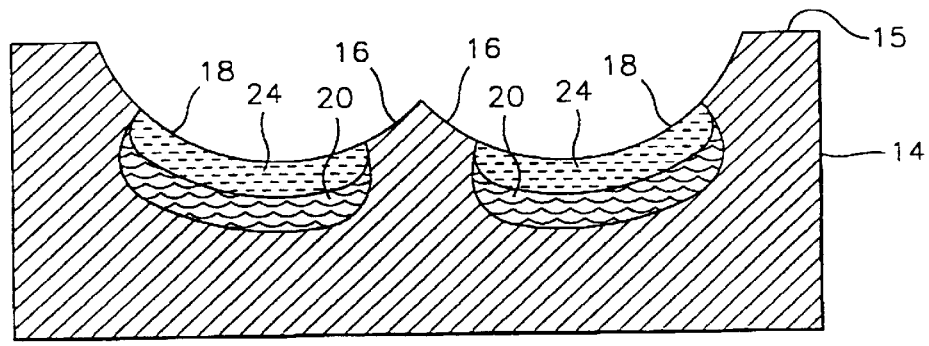

Refer now to FIGS. 4, 5A and 5B wherein the sculpted portion 16 of the support surface 15 on the cushion 14 includes, in the zones 18, an illustrative means for applying cooling in the zones 18 in order to lower the temperature of, and reduce the danger of damage to, the tissue of the weight-bearing areas of the body portion being supported by the cushion 14. In this regard, the cooling means comprise fluid circulating pads 20 through which a cooled fluid can be circulated. Each of the pads includes an inlet hose 21 and an outlet hose 22 through which cooled fluid can be circulated from a source of pressurized, cooled fluid. Cooling pads such as the pads may comprise structures made from two sheets of material, such as flexible polyethylene or polyvinyl films, which are thermo-formed into an array of fluid channels and then heat sealed together around their peripheries.

The cooled fluid is circulated through the pads 20 by an external pump with means for controlling the temperature of the fluid (not shown). The circulating cooled fluid causes each of the fluid circulating pads 20 to be a primary heat sink. Heat is ultimately dissipated into a secondary heat sink (not shown) which is usually at ambient temperature. Connecting the primary heat sink to the secondary heat sink in the instance of the invention illustrated in FIG. 4 requires tubing (provided by the inlet tubes 21 and the outlet tubes 22), a pump, a reservoir, and a cooling means, the latter three not being shown in the figures). The cooling means can comprise compression-based refrigeration, thermo-electric based refrigeration, radiator cooling, ice-based cooling, phase change-based cooling, or any other suitable technology for cooling the circulating fluid.

As best seen in FIG. 5A, the fluid circulating pads 20 each include a surface that is continuous with the surface 15 within the sculpted portion 16. The pads 20 cool the zones 18 when the cooled fluid is circulated through the pads. In FIG. 5A the upper surfaces of the pads 20 come into direct thermal contact with a person. The sculpted portion 16 orients the ischial tuberosities of the person so that they are placed in contact with the cooled zones 18, In FIG. 5B, the fluid circulating pads 20 in the zones 18 are disposed beneath respective layers 24 of thermal conducting material. The layers 24 are optional and are intended to even out any irregularities in the surfaces of the pads 20 caused by thermo-formed channels. Pads filled with liquids or polymeric gels are examples of pads that embody the layers 24.

Figure 6:
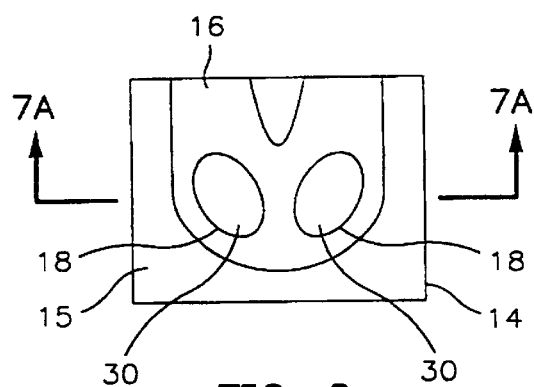
FIG. 6 is a partially schematic illustration of a first alternate embodiment of the support cushion illustrated in FIG. 2.
Figure 7A:
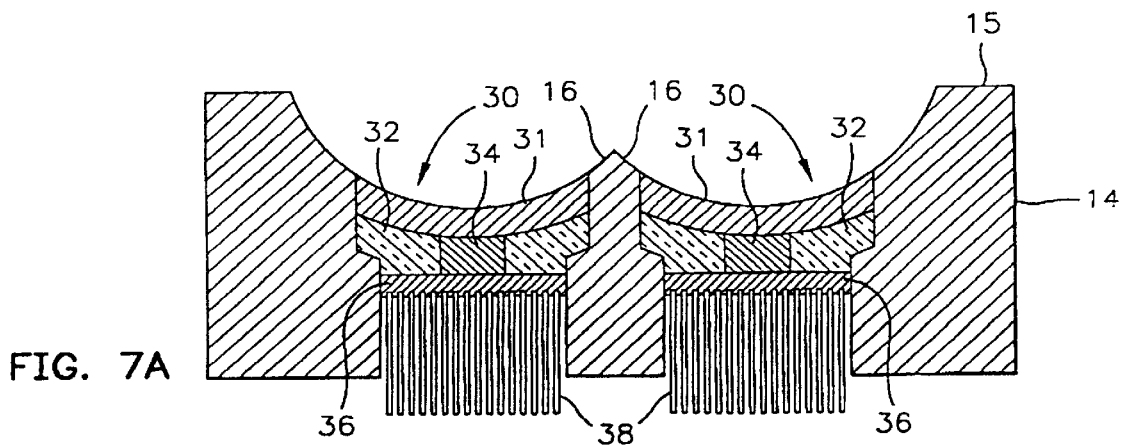
FIGS. 7A and 7B are respective cross-sections taken at C—C of FIG. 6.
Figure 7B:
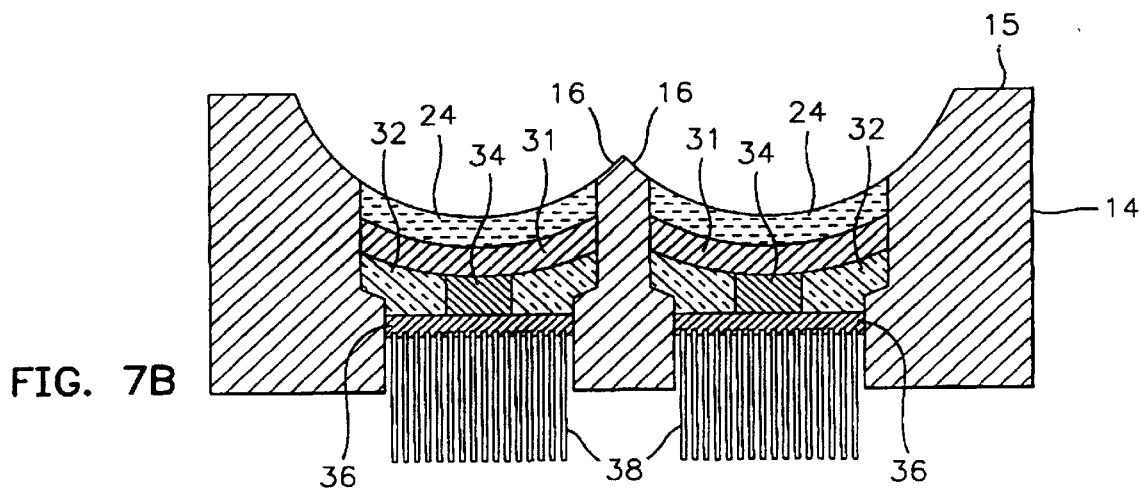

Refer now to FIGS. 6, 7A and 7B for an explanation of a first alternate embodiment of a support cushion according to the invention. In the first alternate embodiment the zones 18 are cooled by thermo-electric devices 30. Each device includes a metal heat sink plate 31 having a contoured upper surface that conforms to and is integrated into the shape of the shaped portion 16 of the support surface 15. A thermal insulator 32 is positioned beneath the heat sink plate 31 and surrounds a thermo-electric module 34. A metal heat radiator plate 36 having a plurality of fins 38 is positioned beneath the thermo-electric module. The thermo-electric module 34 is in intimate thermal contact with the heat sink plate 31 and the metal heat radiator 36 and fins 38. In operation, when a person's buttocks is brought into contact with the contoured upper surface of a heat sink plate 31, heat is conducted from the weight-bearing area of the buttocks through the thermally conductive path 31 34, 36 and is dissipated by the fins 38. Typically, a battery power source and temperature controller (not shown) are provided to operate the thermoelectric module 34. As FIG. 7B shows, the optional thermally conductive pads 24 may be interposed between the upper surfaces of the metal heat sink plates 31 and the body portion being supported by the cushion 14.

Figure 8:
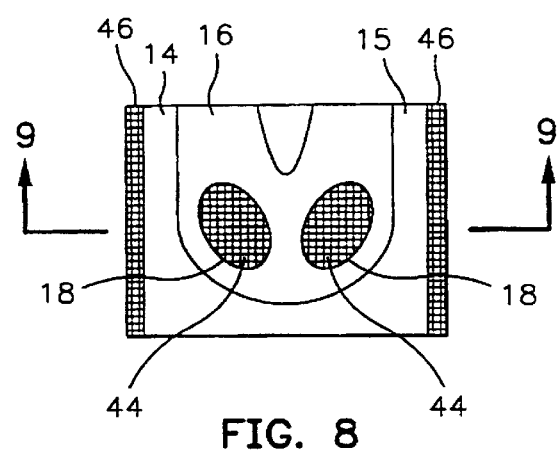
FIG. 8 is a partially schematic illustration of a second alternate embodiment of the support cushion of FIG. 2.
Figure 9:
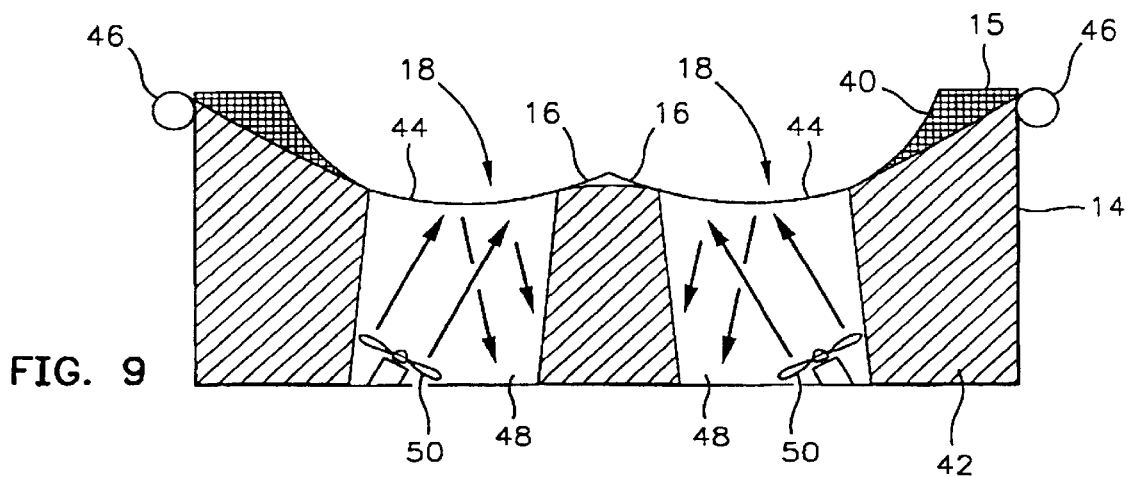
FIG. 9 is a cross-section at D—D of FIG. 8.

FIG. 8 is partially schematic illustration of a second alternate embodiment of the support cushion shown in FIG. 2. In the second alternate embodiment, the cushion 14 comprises two separate sections 40 and 42, with the support surface 15 and shaped portion 16 being formed in the upper section 40. The sections 40 and 42 are brought together, sandwiching a support mesh stretched between two anchoring pipes 46. The zones 18 are defined by two voids 48 that open through the section 42. Preferably, a fan 50 is located below a mesh 44 in each of the voids 48. The fans 50 are positioned to drive cooled, or ambient air toward the meshes 44 at a non-perpendicular angle in order to circulate the air around and through the meshes 44 in the zones 18. The air exits through the meshes 44 and through the bottom of the voids 48. Each mesh 44 is preferably a woven fabric of synthetic, natural, metal or glass fibers, or a combination thereof. Preferably, the meshes 44 are porous, having a loose weave so that air and water vapor can pass through them. The sir circulated around and through the meshes 14 thereby cools the weight-bearing areas of the body portion brought against the zones 18.

Figure 10A:
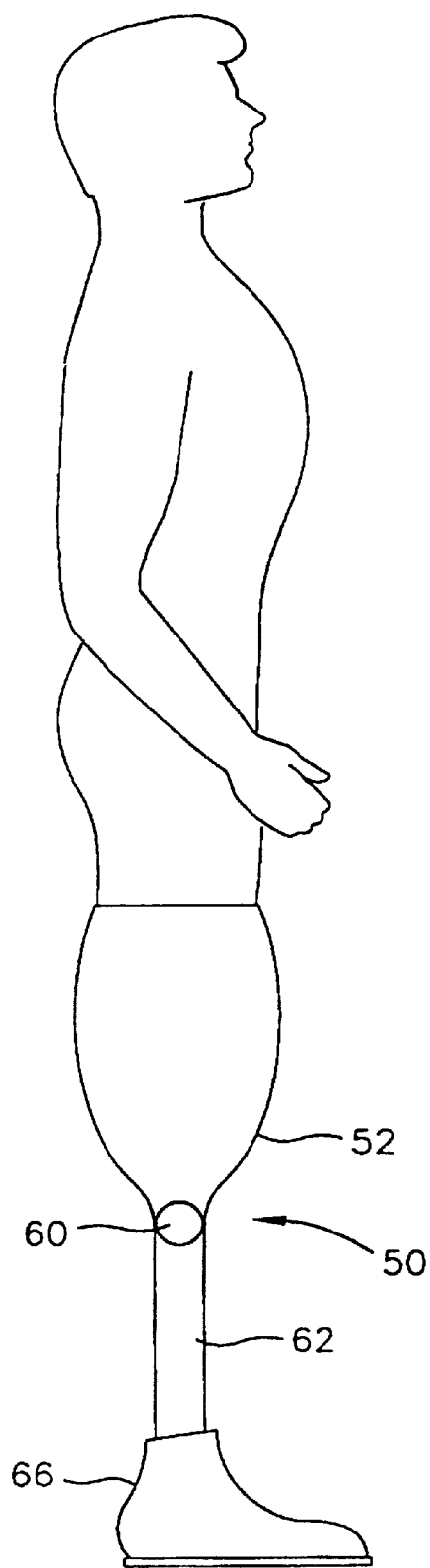
FIGS. 10A and 10B are, respectively, side elevation and side section drawings of a prosthesis that are used to illustrate an environment of the invention.
Figure 10B:
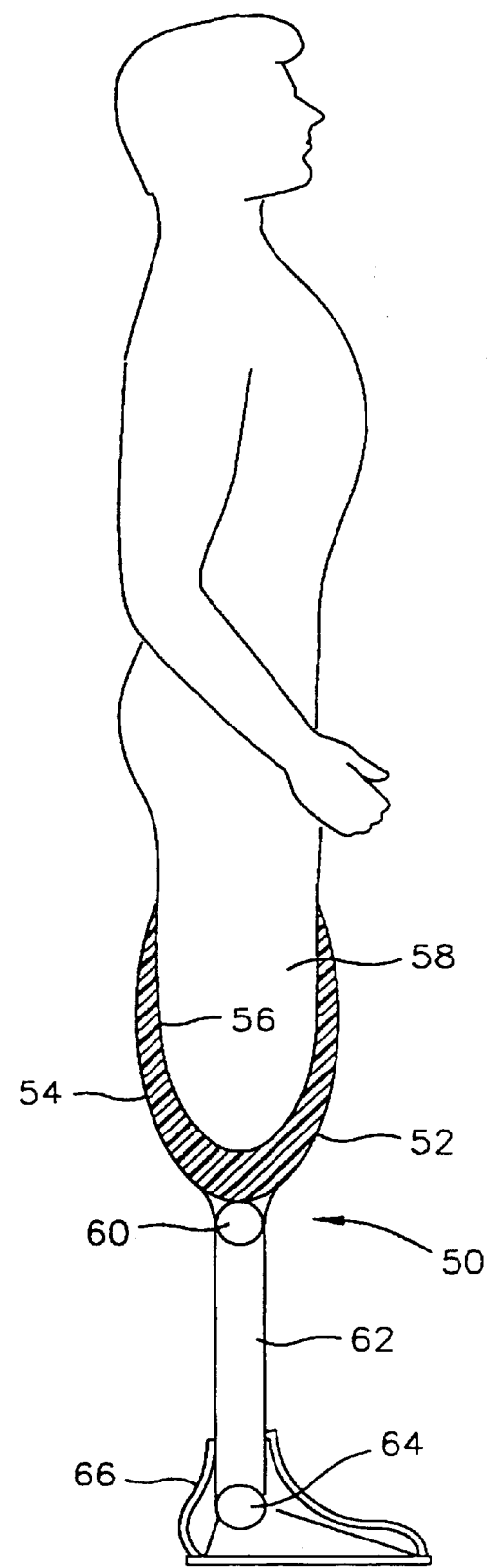

FIGS. 10A and 10B show a side elevation and side sectional view of a standard above-the-knee amputation ("a.k.a.") prosthesis 50. The prosthesis 50 includes a socket 52 having an outer wall surface 54, and having an inner wall surface 56 shaped to receive and fit to the weight-bearing end of a leg stump 5E,. The figures show the stump 58 inserted into and supported by the socket 52 of the prosthesis 50. The socket is attached at its lower end to a knee joint 60, a lower limb segment 62, an ankle joint 64, and a foot 66. A similar socket and prosthesis arrangement is used for below-the-knee amputation ("b.k.a") prosthesis. The socket 52 is typically made of a fiber-reinforced plastic resin (such as fiberglass), which is molded to fit the stump 58.

In addition to the fiberglass socket 52 being an excellent thermal insulator, the stump 58 is usually covered by a thick sock serving as a pad between the stump and the socket 52. Since the end of the femur (upper leg bone) is simply cut off, it is manifest that pressure of a high magnitude is applied to the tissue between the end of the cut femur and the bottom interior of the socket 52. Pressure of such magnitude can cause skin and tissue ischemia and necrosis, creating stump ulcers that are very difficult to heal. Augmenting and accelerating the tissue damage is the heat built up within the socket 52.

Figure 11:
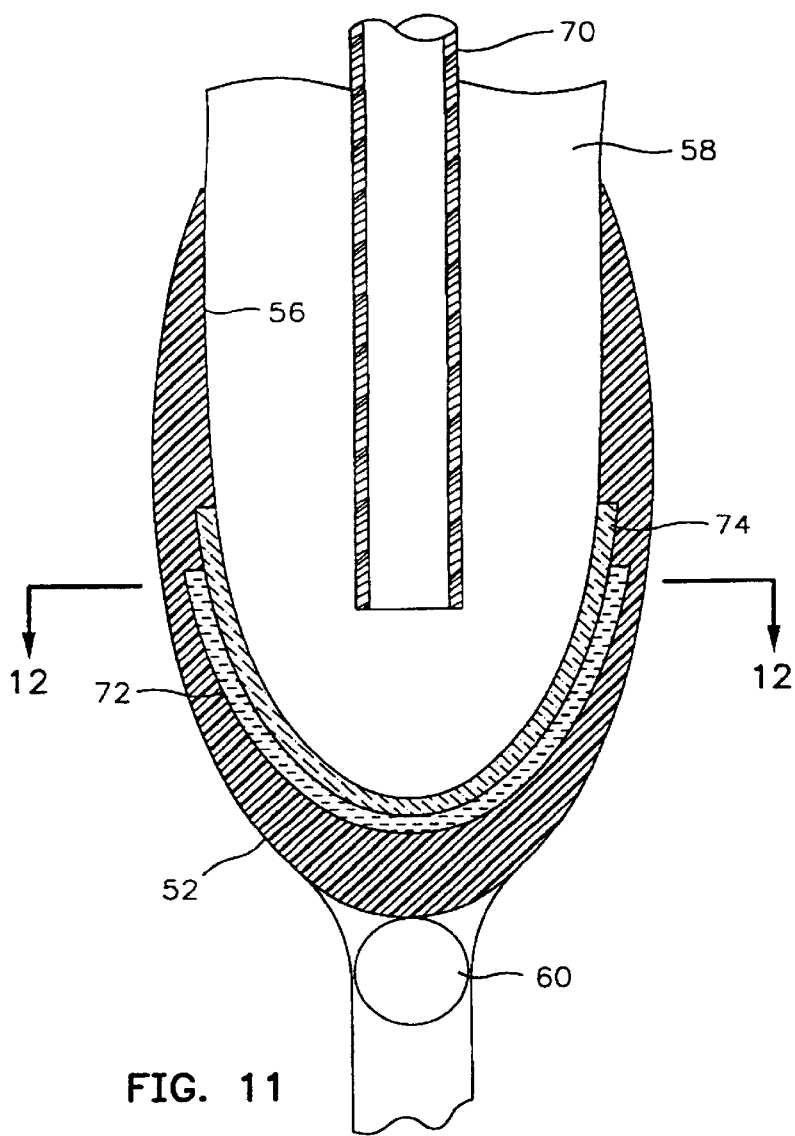
FIG. 11 is a side section drawing illustrating a preferred embodiment of the invention with reference to the side section of FIG. 10B.

FIG. 11 shows a side sectional view of a preferred embodiment of the invention in a prosthesis such as is illustrated in FIGS. 10A and 10B, according to the invention.

Figure 12:
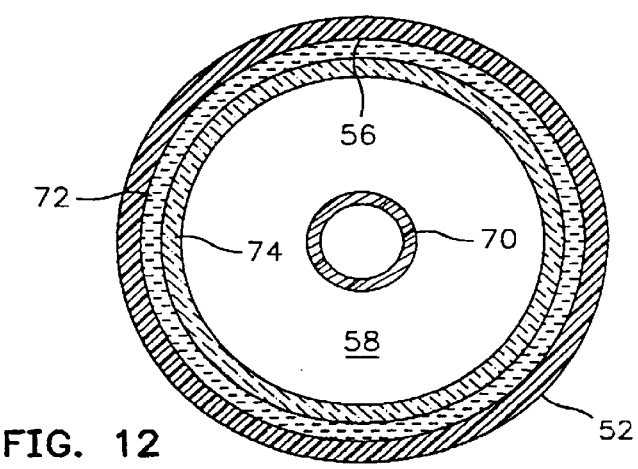
FIG. 12 is a cross sectional view of the preferred embodiment of the prosthesis taken along section E—E in FIG. 11.

The preferred embodiment is also illustrated in FIG. 12, a cross-section taken along E—E of FIG. 11. In FIGS. 11 and 12, the stump 58 is shown with the cut end of the femur 70. It is important to note that there is no bulbous end of the bone 70 as would be seen in a normal joint or a series of bones such as is found in the foot, designed to distribute the weight over a larger area. In the preferred embodiment, the support surface, comprising the inner wall surface 56 is shaped at its lower end to fit to the end of the stump 58. A zone of high pressure between the end of the stump 58 and the inner wall surface 56 of the socket 52 is cooled by a fluid circulating pad 72 corresponding to the pads 20 described above. In this regard, the fluid circulating pad 72 circulates a cooled fluid by conventional means (not shown) and acts as a heat sink, drawing away heat built up in the interface between the end of the stump 58 and the interior of the socket 52. The fluid circulating pad 72 is in thermal contact with the end of the stump 58 either directly, or through a gel- or water-filled pad 74.

Cooled fluid, such as water, is circulated through channels in the pad 72 by, for example, an external pump with cooling capabilities having the characteristics described above in connection with the means for cooling the fluid circulating in the pads 20.

Figure 13:
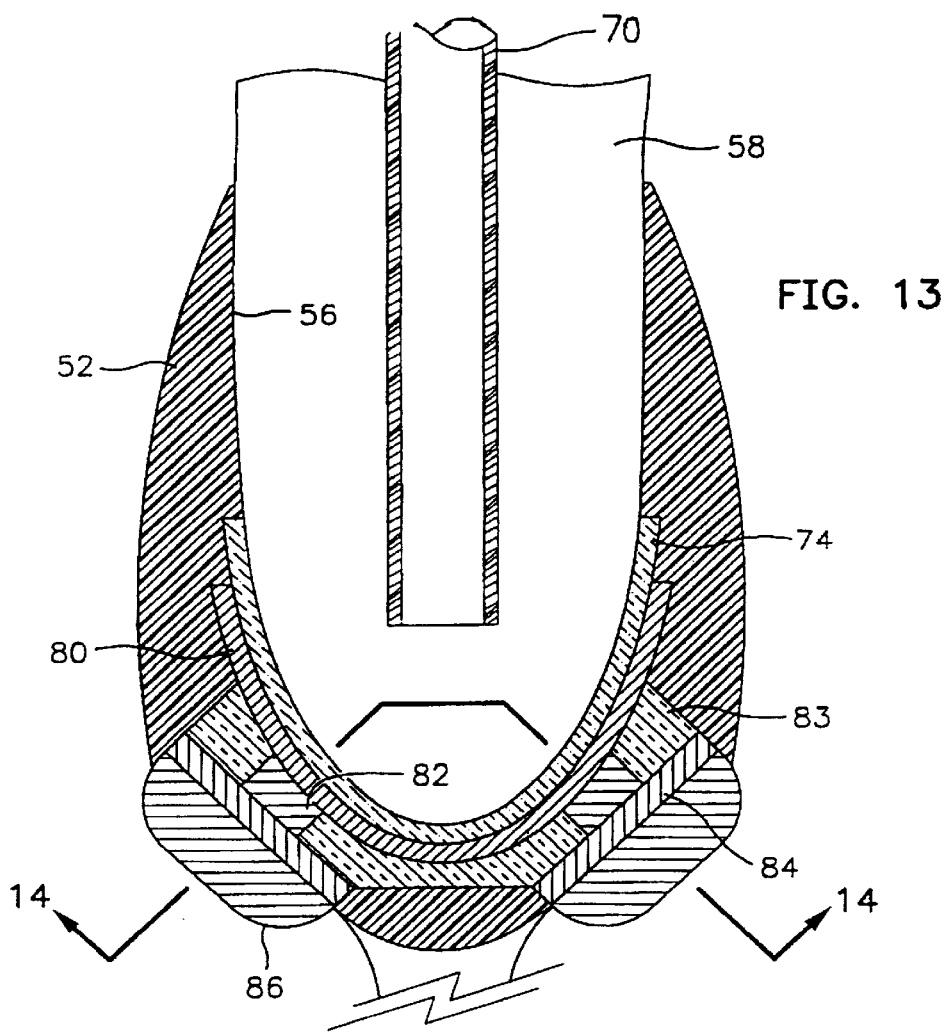
FIGS. 13 and 14 correspond, respectively, to the side arid cross sectional views of FIGS. 11 and 12 and illustrate a first alternate embodiment of the invention.
Figure 14:
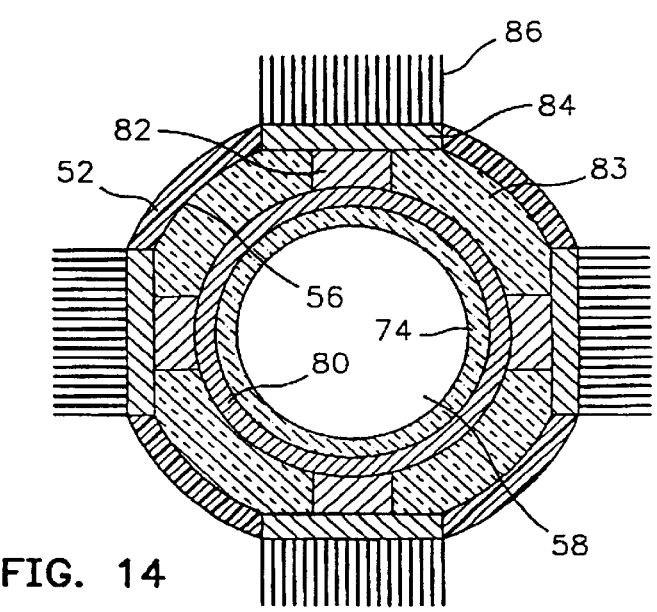

FIG. 13 is a side sectional view of the first alternate embodiment of the prosthesis according to the invention. The first alternate embodiment is also shown in the section illustrated in FIG. 14, which is taken along G—G of FIG. 13. In the first alternate embodiment of the prosthesis according to the invention, the zone to be cooled is defined by the concave upper surface of a metal heat sink plate 80. The concave shape of the upper surface of the plate 80 accommodates the shape of the end of the stump 58. In the illustration of the first alternate embodiment shown in FIGS. 13 and 14, four thermoelectric cooling devices operate to cool the heat sink plate 80. Each thermoelectric device includes a thermoelectric module 82 in intimate thermal contact with the heat sink plate 80 and with a heat radiator plate 84 on which metallic heat radiator fins 86 are mounted. A thermal insulator 83 is provided, for example, by potting material that may be molded to the concave shape of the lower surface of the metal heat sink plate 80. Also shown is the optional thermally-conductive pad 74 comprising a gel- or water-filled cushion.

Figure 15:
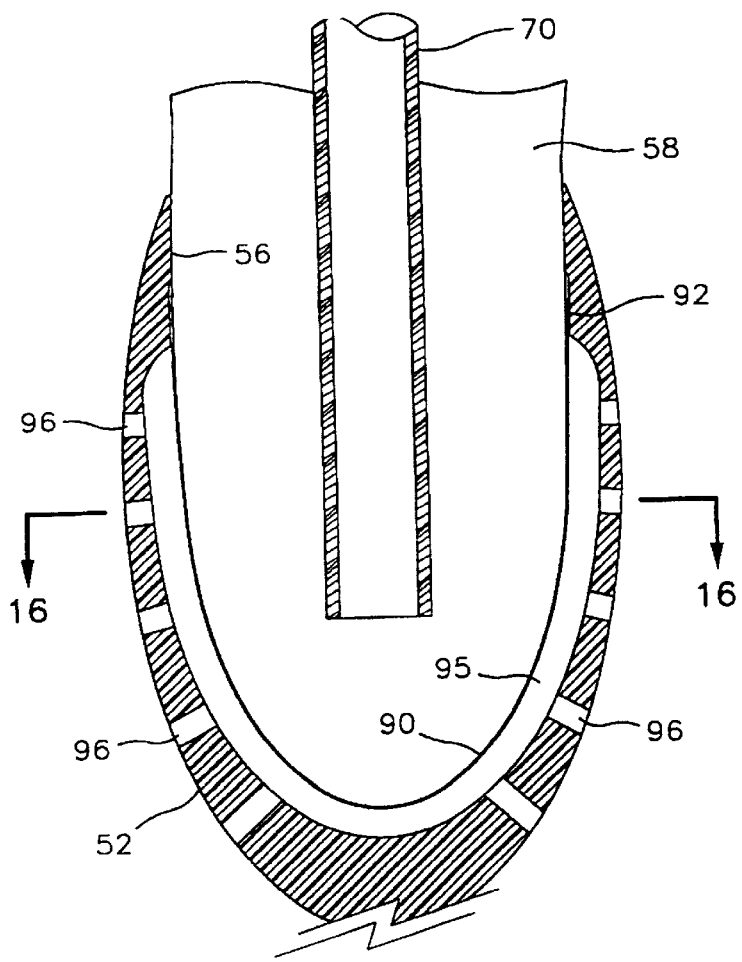
FIGS. 15 and 16 correspond, respectively, to the side and cross sectional views of FIGS. 11 and 12 and illustrate a second alternate embodiment of the invention.
Figure 16:
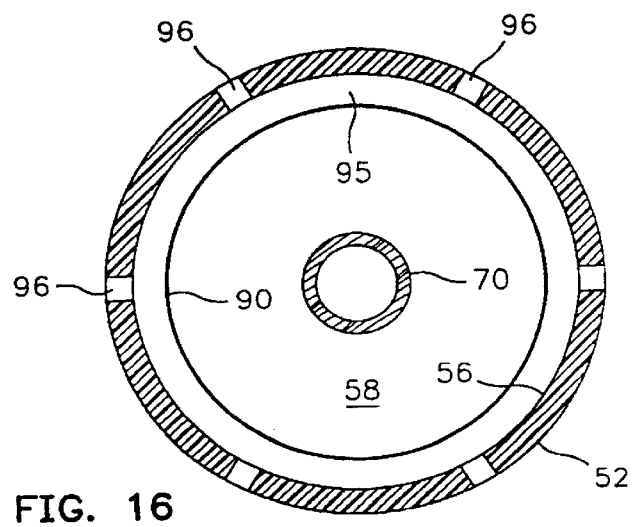

A second alternate embodiment of the prosthesis of the invention is illustrated in FIGS. 15 and 16, in which FIG. 15 is a side sectional view corresponding to FIG. 10B, while FIG. 16 is a cross sectional view taken along I—I in FIG. 15. In the second alternate embodiment, the stump 58 is supported against the inner surface 56 of the socket 52 by a mesh-like material 90 either woven or sewn into the shape of the end of the stump 58. The mesh 90 is preferably porous, having a loose weave permeable by air and water vapor, and may be made of metal, synthetic, natural, or glass fibers, or a combination thereof. The mesh 58 is attached to the inner wall surface 56 along its upper edge by a mesh attachment flange 92. An air space 95 is disposed between the shaped mesh 90 and the interior of the socket 52. The air space 95 is in communication with ambient air through holes 96 through the socket 52. She holes 96 provide natural ventilation between the air space 95 and the ambient atmosphere. With each step, the weight of the person will stretch the mesh 90 and thus force air out of the air space 95. Air will, in turn, be drawn into the air space 95 when the weight is shifted to the other leg, thus creating a natural ventilation. Optionally, a ventilating means such as a fan or fan in combination with a cooler (neither shown in the drawings) may be incorporated to drive cooled air into the air space 95. Cooled air would circulate in the air space 95 and be exhausted through the holes 96 to enable a continuous flow of air through the air space 95.

Obviously, many modifications and variations of the invention will occur to the skilled artisan and may be incorporated into these embodiments without departing from the scope of the invention which is limited only by the following claims.

We claim:

1. An apparatus for supporting at least a portion of a human or animal body ("body portion"), while cooling a weight-bearing area of the body portion, the apparatus comprising:

a weight-bearing article;

a surface on the article;

the surface including a shaped portion corresponding to a shape of the body portion for fitting to the body portion; and at least one cooler positioned to cool a zone of the shaped portion that receives pressure exceeding 20 Torr from a weight-bearing area of the body portion.

2. The apparatus of claim 1, wherein the article is a cushion comprising a compressible material.

3. The apparatus of claim 1, wherein the article is a cushion, the shaped portion being sculpted for fitting to at least the buttocks of a person.

4. The apparatus of claim 3, wherein the at least one cooler includes a fluid circulating pad.

5. The apparatus of claim 4, further including a pad of thermally conductive material between the at least one cooler and the surface.

6. The apparatus of claim 3, wherein the at least one cooler includes a thermoelectric cooling apparatus.

7. The apparatus of claim 6, further including a pad of thermally conductive material between the at least one cooler and the surface.

8. The apparatus of claim 3, wherein the at least one cooler includes means for circulating air through the zone.

9. The apparatus of claim 8, wherein the zone comprises a mesh of permeable material.

10. A cushion for supporting at least a portion of a human or animal body ("body portion"), comprising:
   a surface;
   the surface including a means for cradling the body portion on the surface; and
   means for cooling a zone of the surface that receives pressure exceeding 20 Torr from a weight-bearing area of the body portion.

11. In the cushion of claim 10, wherein the cushion comprises a compressible material.

12. The cushion of claim 10, wherein the means; for cradling includes a shaped portion of the surface corresponding to a shape of the body portion.

13. The cushion of claim 12, wherein the means for cooling includes a fluid circulating pad.

14. The cushion of claim 13, further including a pad of a thermally-conductive material between the fluid circulating pad and the surface.

15. The cushion of claim 12, wherein the means for cooling includes a thermoelectric cooling apparatus.

16. The cushion of claim 15, further including a pad of thermally-conductive material between the thermo-electric cooling apparatus and the surface.

17. The cushion of claim 12, wherein the means for cooling includes means for circulating air through the zone.

18. The apparatus of claim 17, wherein the zone comprises a mesh of permeable material.

19. A method for supporting a body on a weight-bearing article that includes a surface with a shaped portion that corresponds to a shape of a portion of the body, while selectively cooling areas of the body in contact with the article, comprising the steps of:
   receiving a portion of the body ("body portion") in the shaped portion of the surface; and
   cooling one or more zones of the shaped portion of the surface, each zone receiving pressure exceeding 20 Torr from a weight-bearing area of the body portion.

* * * * *